US012629489B2

(12) United States Patent
Lee et al.

(10) Patent No.: US 12,629,489 B2
(45) Date of Patent: May 19, 2026

(54) CONTINUOUS POSITIVE AIRWAY PRESSURE DEVICE

(71) Applicant: GrowTrend Biomedical Co., Ltd., Hsinchu City (TW)

(72) Inventors: Chin-Ni Lee, New Taipei City (TW); Pei-Yin Ou, New Taipei City (TW); Neng Yu Pan, New Taipei City (TW); Ching-Liang Yu, Taoyuan City (TW)

(73) Assignee: GROWTREND BIOMEDICAL CO., LTD., Hsinchu City (TW)

( * ) Notice: Subject to any disclaimer, the term of this patent is extended or adjusted under 35 U.S.C. 154(b) by 634 days.

(21) Appl. No.: 18/134,644

(22) Filed: Apr. 14, 2023

(65) Prior Publication Data

US 2023/0338678 A1      Oct. 26, 2023

(30) Foreign Application Priority Data

Apr. 20, 2022    (TW) .................................. 111204032

(51) Int. Cl.
*A61M 16/00*        (2006.01)
*F04D 29/66*        (2006.01)

(52) U.S. Cl.
CPC ....... *A61M 16/0066* (2013.01); *F04D 29/664* (2013.01); *A61M 2016/0039* (2013.01); *A61M 2205/42* (2013.01); *A61M 2206/11* (2013.01)

(58) Field of Classification Search
CPC ........... A61M 16/0066; A61M 16/0069; F04D 29/664
See application file for complete search history.

(56) References Cited

U.S. PATENT DOCUMENTS

| | | | | |
|---|---|---|---|---|
| 6,216,691 B1 * | 4/2001 | Kenyon | .................. | F01C 21/10 128/205.18 |
| 7,617,823 B2 * | 11/2009 | DiMatteo | .............. | F04D 29/664 128/204.21 |
| 2009/0007912 A1 * | 1/2009 | Lindell | ................. | A61M 16/10 128/204.18 |
| 2012/0037160 A1 * | 2/2012 | Sung | ...................... | F04D 25/08 128/205.12 |

(Continued)

FOREIGN PATENT DOCUMENTS

| | | |
|---|---|---|
| WO | 9922794 | 5/1999 |
| WO | 2005/097244 | 10/2005 |
| WO | 2020/121255 | 6/2020 |

*Primary Examiner* — Bradley H Philips
(74) *Attorney, Agent, or Firm* — Birch, Stewart, Kolasch & Birch, LLP

(57) ABSTRACT

A continuous positive airway pressure device has a shell, a diversion sound-absorbing foam pad, a blower, and a partition. The shell has an inlet and an outlet. The diversion sound-absorbing foam pad is disposed inside the shell and forms an airflow passage extending tortuously inside the shell. The blower is disposed on the diversion sound-absorbing foam pad and fluidly communicates with the airflow passage and the outlet of the shell. The partition covers the blower and the diversion sound-absorbing foam pad and has a leading hole fluidly communicating with the airflow passage and the inlet of the shell. After air flows into an interior space of the shell, the air flows through the airflow passage being tortuous and then flows out from the shell, which lengthens flow path of the air, reduces noises generated during the air flowing, and helps the air to flow more fluently.

17 Claims, 10 Drawing Sheets

(56)         References Cited

U.S. PATENT DOCUMENTS

2016/0325059 A1* 11/2016 Cheng .............. A61M 16/0057
2017/0203064 A1    7/2017 Suzuki et al.
2023/0338681 A1* 10/2023 Li ........................ F04D 29/664

* cited by examiner

CONTINUOUS POSITIVE AIRWAY PRESSURE DEVICE

BACKGROUND OF THE INVENTION

1. Field of the Invention

The present invention relates to a respirator, and particularly to a continuous positive airway pressure device.

2. Description of Related Art

A conventional respirator, particularly a conventional continuous positive airway pressure device, mainly has a shell, and an inlet and an outlet are defined through the shell. The conventional continuous positive airway pressure device has a fan disposed inside the shell. Since a portion of the shell around the inlet is normally smooth, air outside the shell quickly flows through the inlet into an interior of the shell, wherein most portion of the air flows into the fan from a middle of a top of the fan, is compressed and pushed, and flows outside the shell from the outlet, and the other portion of the air flows through a gap between the fan and a portion of the shell near the inlet.

However, since the conventional continuous positive airway pressure device has a small volume, a flow path of the air from the inlet, through the fan, and to the outlet is short, and furthermore the portion of the air flowing through the opening makes shrill and annoying noises. Thereby, users may feel uncomfortable after applying the conventional continuous positive airway pressure device for a period of time and may even have low sleep quality when applying it during sleep.

To overcome the shortcomings of the conventional continuous positive airway pressure device, the present invention tends to provide a continuous positive airway pressure device to mitigate or obviate the aforementioned problems.

SUMMARY OF THE INVENTION

The main objective of the present invention is to provide a continuous positive airway pressure device that has a diversion sound-absorbing foam pad and a partition to lengthen a flow path of air and reduce noises in use.

The continuous positive airway pressure device has a shell, a diversion sound-absorbing foam pad, a blower, and a partition. The shell has an upper shell body, a lower shell body connected to the upper shell body, an interior space, and an inlet and an outlet both fluidly communicating with the interior space of the shell. The diversion sound-absorbing foam pad is disposed in the interior space of the shell and has a bottom board, a first side wall, a second side wall, a third side wall, and a fourth side wall. The first side wall, the second side wall, the third side wall, and the fourth side wall protrude from the bottom board, are sequentially arranged, and enclose a containing space of the diversion sound-absorbing foam pad. The diversion sound-absorbing foam pad has a blower seat protruding from the bottom board, disposed in the containing space, and having an opening. The opening is recessed on the blower seat, fluidly communicates with the containing space, and is disposed near the fourth side wall. The diversion sound-absorbing foam pad forms an airflow passage, and the airflow passage extends tortuously inside the shell and around the diversion sound-absorbing foam pad, sequentially passes by a top surface of the first side wall, a top surface of the second side wall, two opposite ends of the third side wall, and the fourth side wall, and fluidly communicates with the opening. The blower is disposed in the containing space, is disposed on the blower seat, and has a blower fluid inlet and a blower fluid outlet. The blower fluid inlet fluidly communicates with the opening of the blower seat, and the blower fluid outlet fluidly communicates with the outlet of the shell. The partition is fixed on the lower shell body, covers the blower and the diversion sound-absorbing foam pad, and has a leading hole. The leading hole is defined through the partition, fluidly communicates with a portion of the airflow passage near the first side wall, and fluidly communicates with the inlet of the shell.

Other objectives, advantages and novel features of the invention will become more apparent from the following detailed description when taken in conjunction with the accompanying drawings.

DETAILED DESCRIPTION OF THE PREFERRED EMBODIMENT

Figure 1:
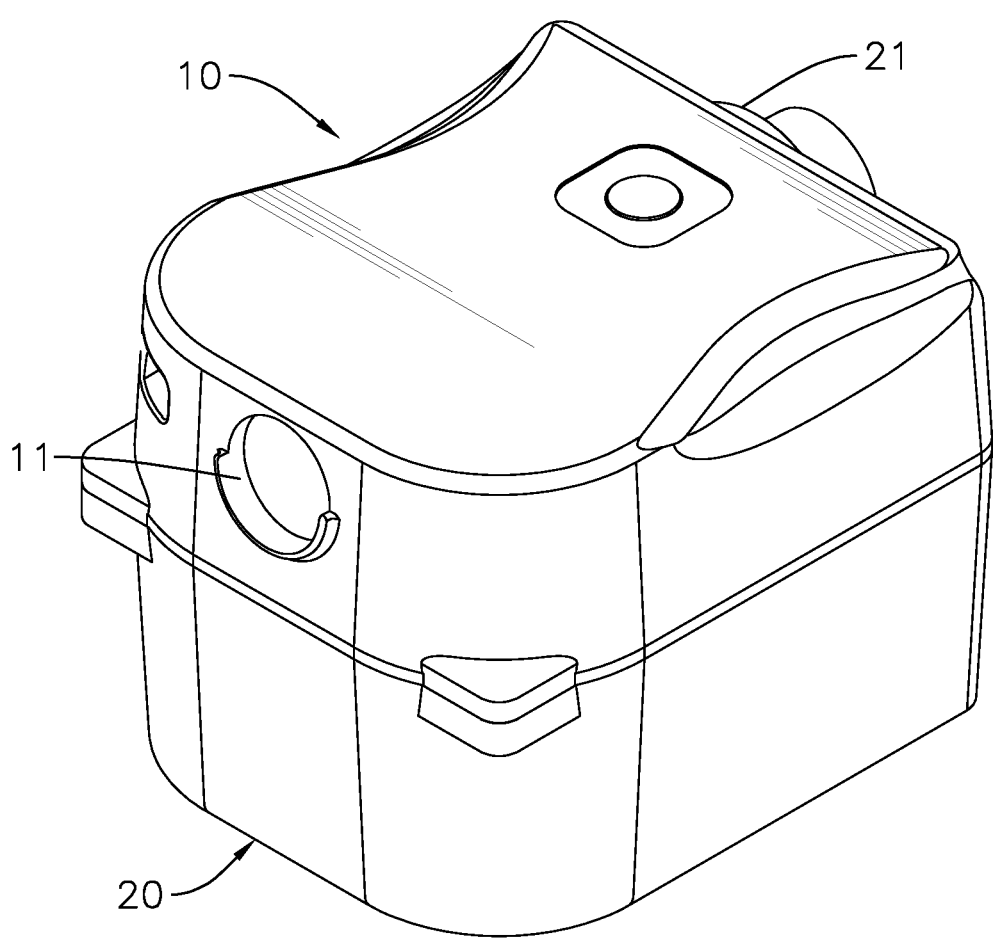
FIG. 1 is a perspective view of a continuous positive airway pressure device of a preferred embodiment in accordance with the present invention.
Figure 2:
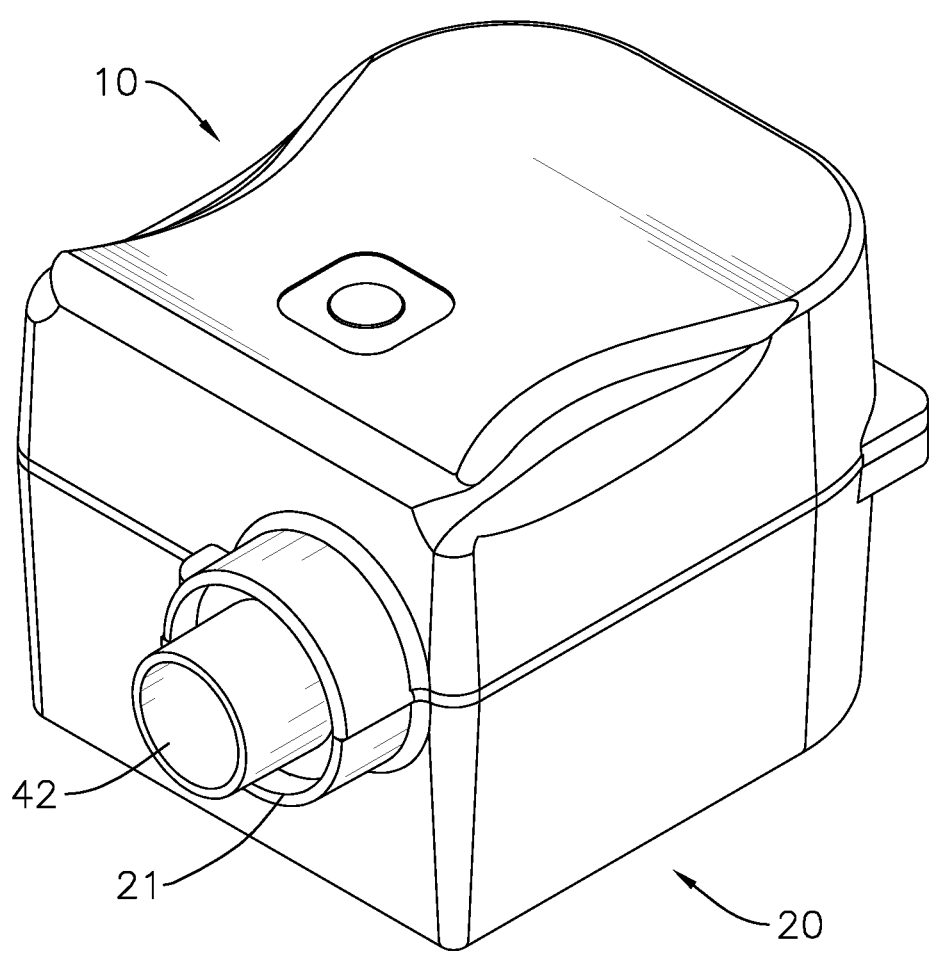
FIG. 2 is another perspective view of the continuous positive airway pressure device in FIG. 1.
Figure 3:
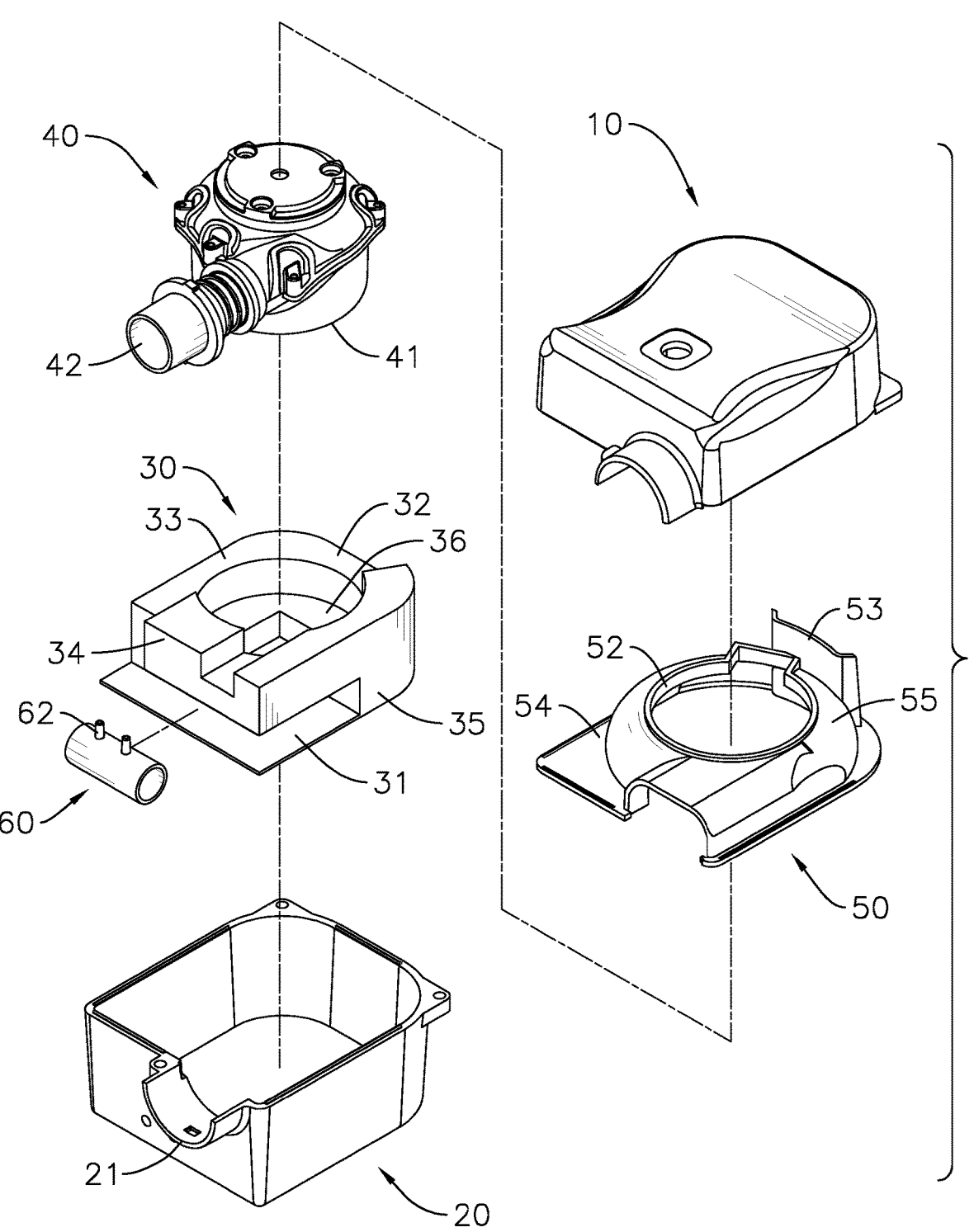
FIG. 3 is an exploded view of the continuous positive airway pressure device in FIG. 1.

With reference to FIGS. 1 to 3, a continuous positive airway pressure device of a preferred embodiment in accordance with the present invention has a shell having an upper shell body 10 and a lower shell body 20, a diversion sound-absorbing foam pad 30, a blower 40, a partition 50, and a fluid rectifier 60.

With reference to FIGS. 1 to 3, the upper shell body 10 and the lower shell body 20 are connected to each other to form the shell. The shell encloses an interior space, an inlet 11, and an outlet 21, and the inlet 11 and the outlet 21 are respectively located at two opposite sides of the shell.

With reference to FIGS. 3, 4, 9, and 10, the diversion sound-absorbing foam pad 30 is made of a foam material and has a bottom board 31, a first side wall 32, a second side wall 33, a third side wall 34, and a fourth side wall 35. The bottom board 31 is disposed inside the lower shell body 20. The first side wall 32, the second side wall 33, the third side wall 34, and the fourth side wall 35 protrude from the bottom board 31, are arranged sequentially, and enclose a containing space of the diversion sound-absorbing foam pad 30. The diversion sound-absorbing foam pad 30 has a blower seat 36 protruding from the bottom board 31 and disposed inside the containing space. The blower seat 36 has an opening 361 recessed on a side of the blower seat 36 near the fourth side wall 35, and the opening 361 extends inward and roughly to a center of the blower seat 36 and fluidly communicates with the containing space of the diversion sound-absorbing foam pad 30.

With reference to FIGS. 3, 4, and 8 to 10, the first side wall 32, the second side wall 33, the third side wall 34, and the fourth side wall 35 of the diversion sound-absorbing foam pad 30, the upper shell body 10, and the lower shell body 20 together enclose an airflow passage. The first side wall 32, the second side wall 33, and the fourth side wall 35 are tightly attached to an internal wall of the lower shell body 20. An upper portion of the third side wall 34 is tightly attached to the internal wall of the lower shell body 20, and a lower end portion of the third side wall 34 is spaced from the internal wall of the lower shell body 20. The airflow passage extends tortuously inside the shell and around the diversion sound-absorbing foam pad 30 and sequentially passes by a top surface of the first side wall 32, a top surface of the second side wall 33, two opposite ends of the third side wall 34, and the fourth side wall 35. Specifically, the airflow passage extends curvedly from the top surface of the first side wall 32 to the top surface of the second side wall 33, extends downward from the top surface of the second side wall 33, and then bends at one of the two opposite ends of the third side wall 34; then, the airflow passage extends toward the other one of the two opposite ends of the third side wall 34, extends from the third side wall 34 to the fourth side wall 35, and fluidly communicates with the opening 361.

Figure 8:
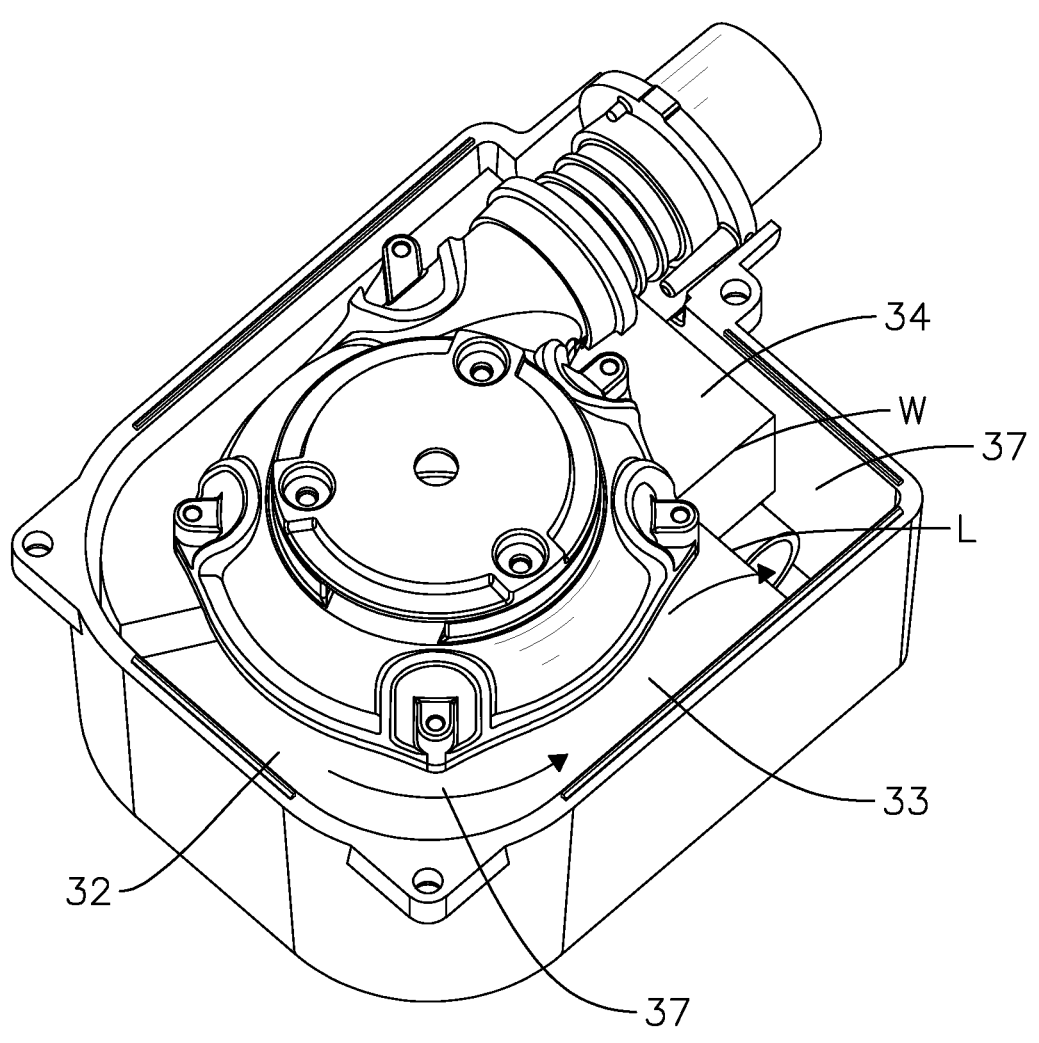
Figure 9:
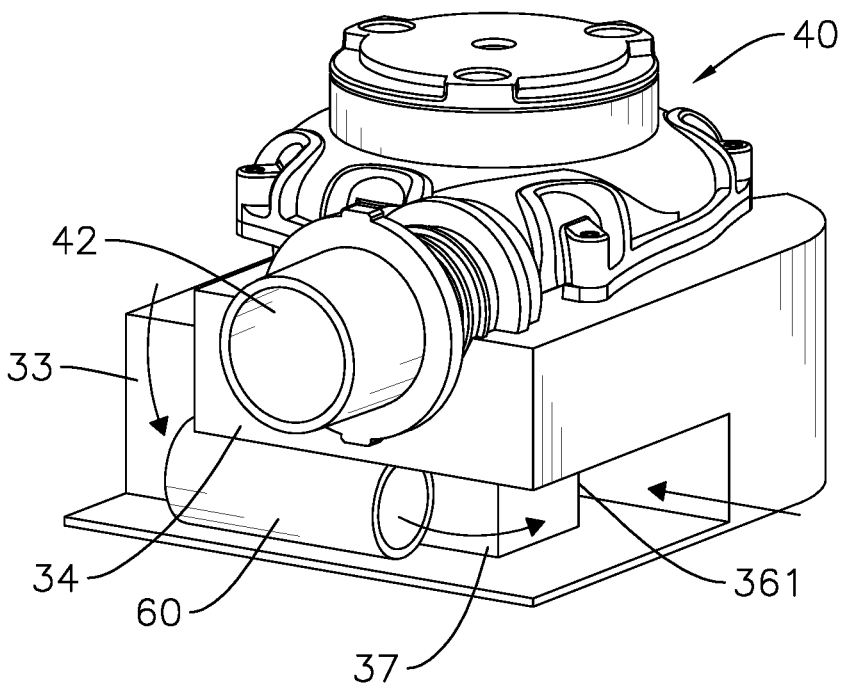
Figure 10:
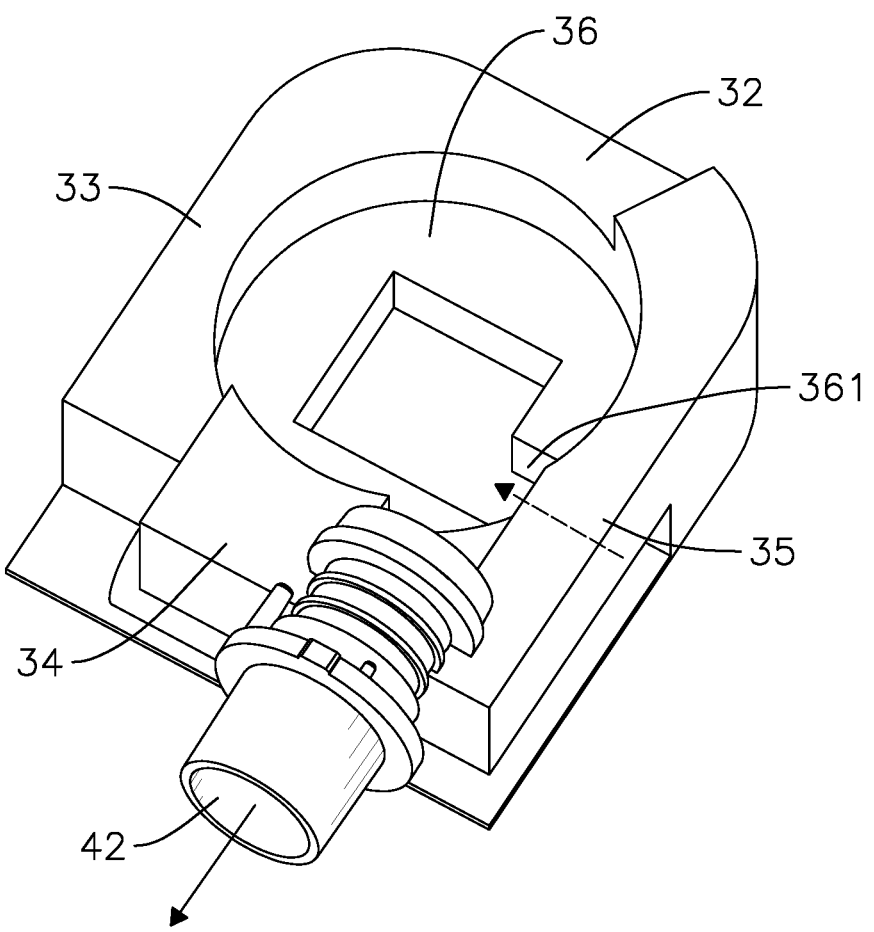

With reference to FIGS. 8 and 9, in the preferred embodiment, the airflow passage has multiple flow openings 37, and the multiple flow openings 37 are respectively located between the first side wall 32 and the second side wall 33 (an opening for airflow to flow from the top surface of the first side wall 32 to the top surface of the second side wall 33), between the second side wall 33 and the third side wall 34, and between the third side wall 34 and the fourth side wall 35. With reference to FIG. 8, each one of the multiple flow openings 37 is rectangular and has two length edges L and two width edges W. A ratio of a length of said length edge L to a length of said width edge W, simply regarded as a length-width ratio, is preferably between 1:0.4 and 1:0.7, but the present invention is not limited to the above disclosure; configurations of the diversion sound-absorbing foam pad 30 may change according to needs of users in other embodiments.

Figure 4:
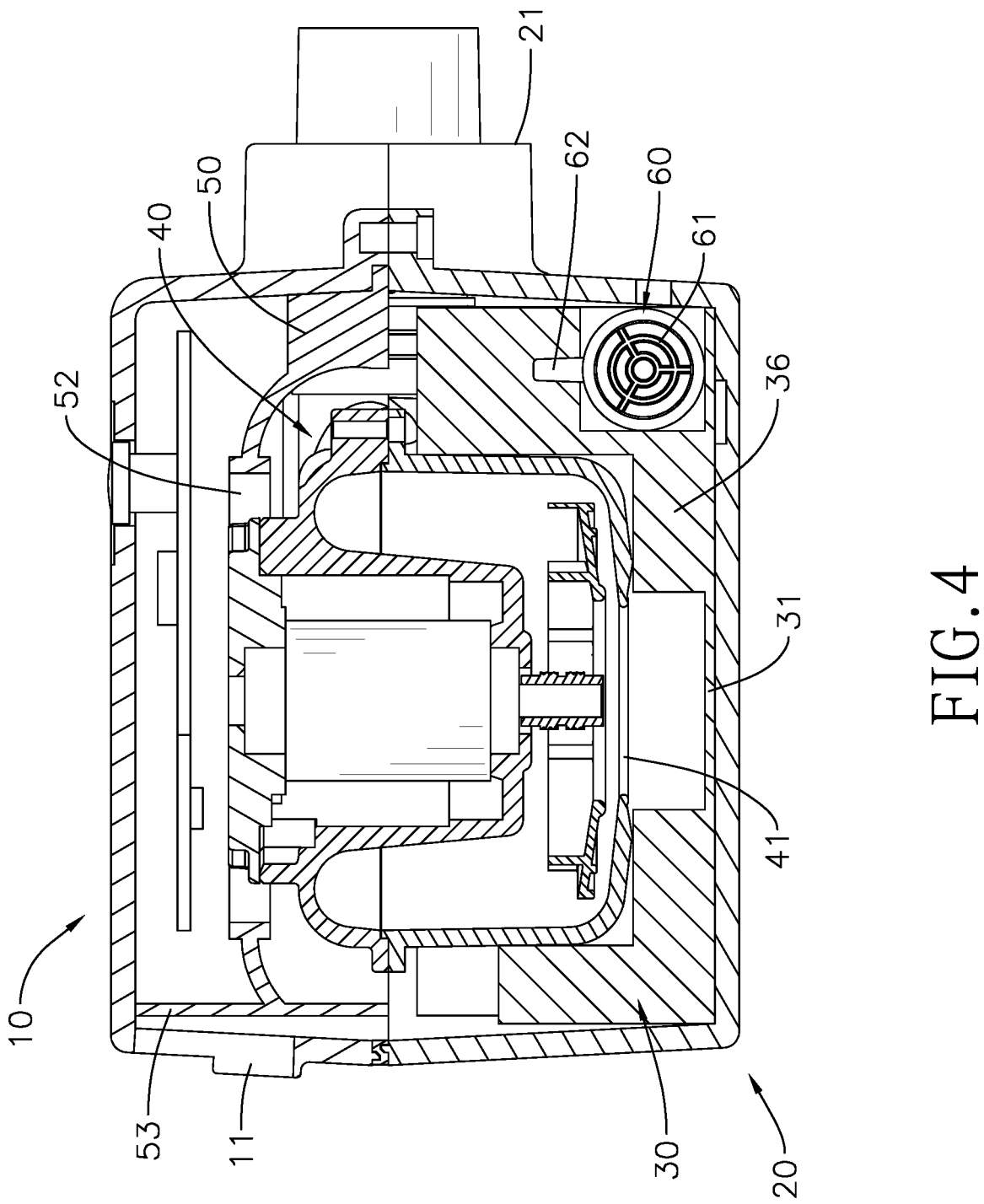
FIG. 4 is a sectional side view of the continuous positive airway pressure device in FIG. 1.

With reference to FIGS. 3 and 4, the blower 40 has a blower fluid inlet 41 and a blower fluid outlet 42. The blower 40 is disposed on the blower seat 36, and the blower fluid inlet 41 of the blower 40 fluidly communicates with the opening 361 of the blower seat 36. The blower fluid outlet 42 is located through the outlet 21 of the shell. The blower 40 is conventional, and thus detailed constructions of the blower 40 are not described.

Figure 5:
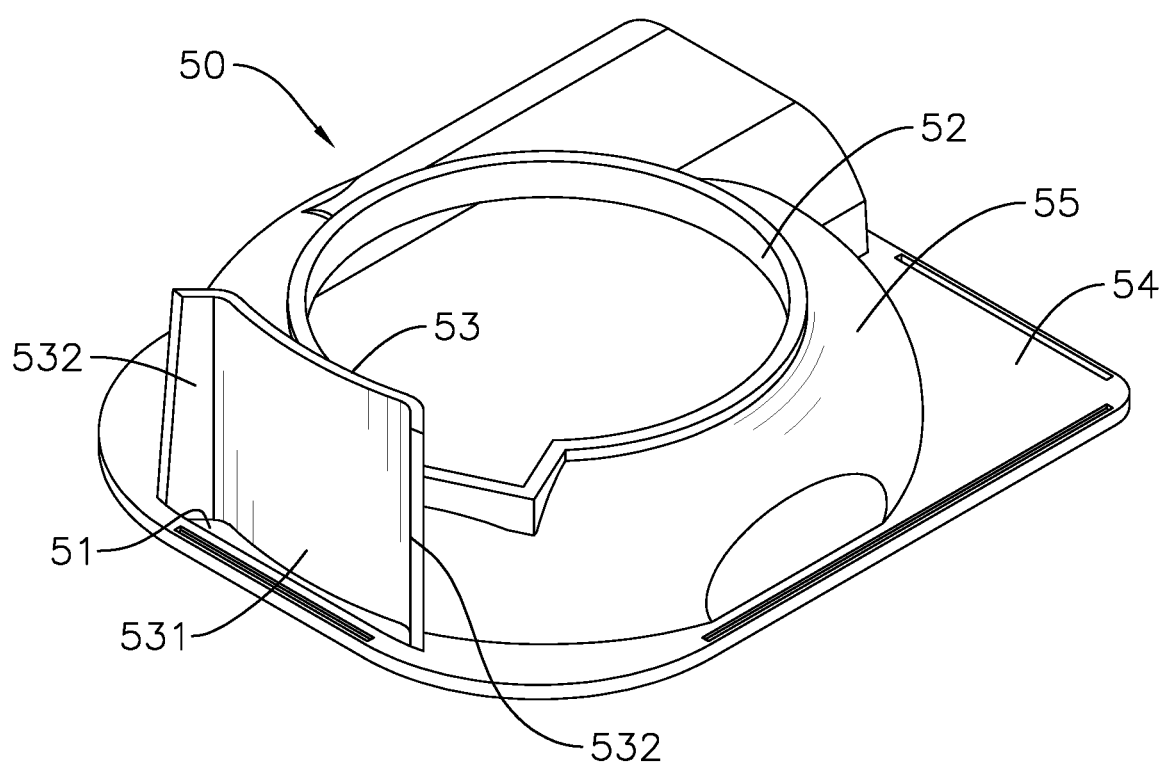
FIG. 5 is a perspective view of a partition of the continuous positive airway pressure device in FIG. 1.
Figure 6:
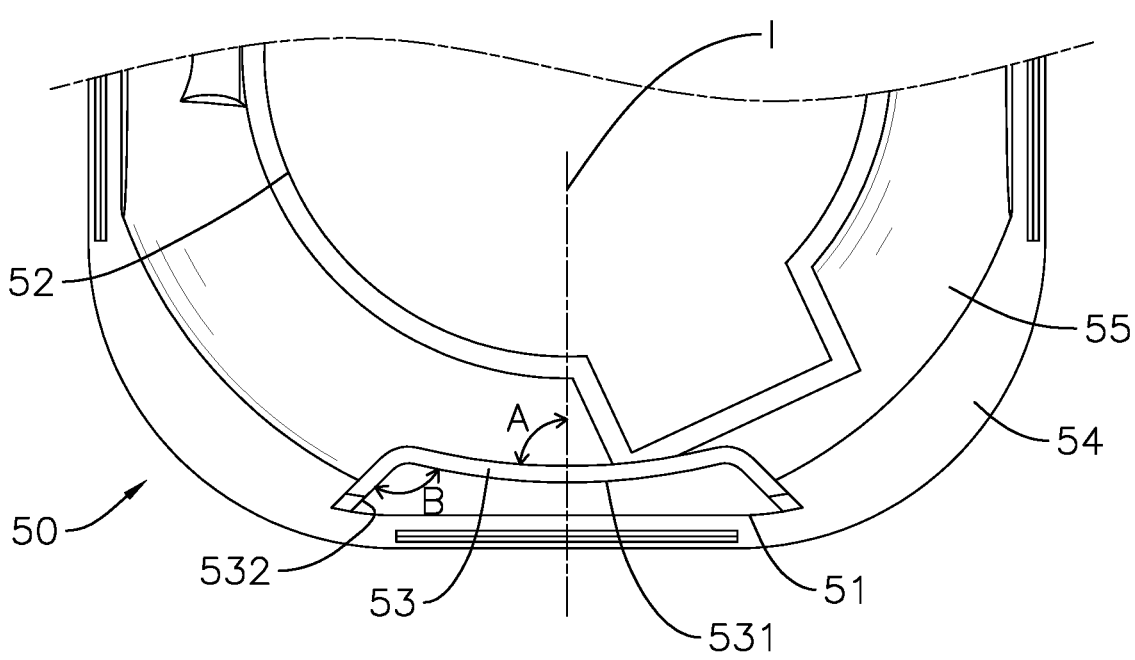
FIG. 6 is a partial enlarged view of the partition in FIG. 5.
Figure 7:
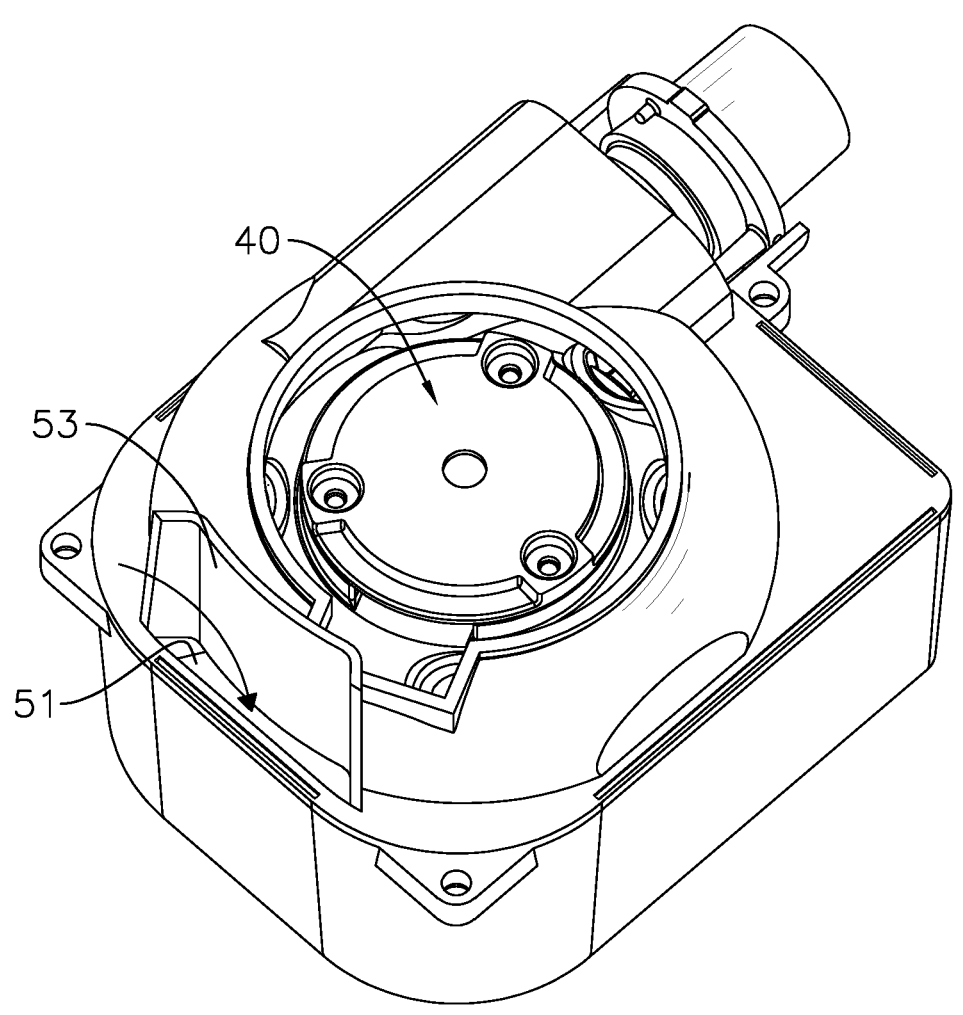
FIGS. 7 to 10 depict a flow path of air in the continuous positive airway pressure device in FIG. 1.

With reference to FIGS. 3, 5, and 6, the partition 50 has a shape corresponding to a shape of a cover body of the blower 40, and the partition 50 has a leading hole 51 and a heat dissipating hole 52 both defined through the partition 50. The partition 50 covers the blower 40 and the diversion sound-absorbing foam pad 30, and the leading hole 51 fluidly communicates with the inlet 11 of the shell and a portion of the airflow passage near the first side wall 32. In the preferred embodiment, the partition 50 has a dissipating cover 55, a surrounding bottom board 54, and a leading board 53. The surrounding bottom board 54 is annularly connected to a surrounding edge of the heat dissipating cover 55, and the leading hole 51 is defined through the surrounding bottom board 54. The leading board 53 protrudes from a position of the surrounding bottom board 54 near the leading hole 51.

With reference to FIG. 6, the leading board 53 has two opposite side surfaces, and one of the two opposite side surfaces of the leading board 53 is disposed toward the leading hole 51 and is defined as a central surface 531. The central surface 531 is a convex surface curved toward the leading hole 51 and has a central line. The central line is configured to define an imaginary vertical surface I, and a first angle A is defined between the imaginary vertical surface I and the other one of the two opposite side surfaces of the leading board 53. The first angle A is preferably between 70 degrees and 89 degrees. The leading board 53 has two end surfaces 532, and each one of the two end surfaces 532 extends outward from a respective one of two opposite side edges of the central surface 531. Each one of the two end surfaces 532 is configured to define a second angle B between said end surface 532 and the central surface 531, and the second angle B is preferably between 90 degrees and 140 degrees.

With reference to FIGS. 3 and 4, a position of the heat dissipating hole 52 corresponds to a position of the blower 40 and the heat dissipating hole 52 is configured for heat dissipation of the blower 40. The partition 50 is fixed on an upper edge of the lower shell body 20 to cover the blower 40 and the diversion sound-absorbing foam pad 30. In other embodiments, configurations of the partition 50 and its leading board 53 may change according to needs of the users and are not limited to the preferred embodiment.

With reference to FIGS. 3 and 4, the fluid rectifier 60 is a hollow tube and has multiple surrounding walls 61 disposed in an interior of the fluid rectifier 60. The multiple surrounding walls 61 are arranged at spaced intervals and divide the interior of the fluid rectifier 60 into multiple passages. The continuous positive airway pressure device further has at least one detector 62 disposed to the fluid rectifier 60 and configured to detect flow volume and flow velocity of airflow in the fluid rectifier 60. In the preferred embodiment, the fluid rectifier 60 is disposed in the airflow passage and is disposed between the internal wall of the lower shell body 20, the third side wall 34, and the bottom board 31. In other embodiments, configurations and position of the fluid rectifier 60 may change according to needs of the users and are not limited to the preferred embodiment.

In use of the continuous positive airway pressure device, with reference to FIGS. 1, 3, and 7 to 10, direction of airflow is illustrated by arrows in the figures. The blower 40 makes air outside the shell flow into the continuous positive airway pressure device from the inlet 11 of the shell, and the air is then led by the leading board 53 to flow downward into the airflow passage from the leading hole 51. Afterwards, the air flows by said top surfaces of the first side wall 32 and the second side wall 33, flows downward through said flow opening 37 between the second side wall 33 and the third side wall 34, and flows into the fluid rectifier 60 from one of two opposite ends of the fluid rectifier 60. Then, the air flows out from the other one of the two opposite ends of the fluid rectifier 60 and flows through the opening 361 near the fourth side wall 36. Finally, the air enters the blower 40 from the blower fluid inlet 41 and flows out from the blower fluid outlet 42. By multiple bends in the flowing path of the air in the continuous positive airway pressure device described above, noises generated while the air flows are apparently reduced, and muting effect of the continuous positive airway pressure device can be improved.

In the above description of the preferred embodiment, the smooth and curved surface on the leading board 53 and the multiple passages formed inside the fluid rectifier 60 are both configured to adjust airflow and help the air to flow more fluently in the continuous positive airway pressure device of the present invention.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A continuous positive airway pressure device comprising:

a shell having
      an upper shell body;
      a lower shell body connected to the upper shell body;
      an interior space; and
      an inlet and an outlet both fluidly communicating with the interior space of the shell;
   a diversion sound-absorbing foam pad disposed in the interior space of the shell and having
      a bottom board;
      a first side wall, a second side wall, a third side wall, and a fourth side wall protruding from the bottom board and arranged sequentially;
      a containing space enclosed by the first side wall, the second side wall, the third side wall, and the fourth side wall; and
      a blower seat protruding from the bottom board, disposed in the containing space, and having
         an opening recessed inward on the blower seat, fluidly communicating with the containing space, and disposed near the fourth side wall; and
      wherein the diversion sound-absorbing foam pad forms an airflow passage, and the airflow passage extends tortuously inside the shell and around the diversion sound-absorbing foam pad, sequentially passes by a top surface of the first side wall, a top surface of the second side wall, two opposite ends of the third side wall, and the fourth side wall, and fluidly communicates with the opening;
   a blower disposed in the containing space, disposed on the blower seat, and having
      a blower fluid inlet fluidly communicating with the opening of the blower seat of the diversion sound-absorbing foam pad; and
      a blower fluid outlet fluidly communicating with the outlet of the shell; and
   a partition fixed on a top edge of the lower shell body, covering the blower and the diversion sound-absorbing foam pad, and having
      a leading hole defined through the partition, fluidly communicating with a portion of the airflow passage near the first side wall, and fluidly communicating with the inlet of the shell.

2. The continuous positive airway pressure device as claimed in claim 1, wherein the partition has
      a heat dissipating cover having a surrounding edge;
      a surrounding bottom board annularly connected to the surrounding edge; and
      a leading board protruding from a position of the surrounding bottom board near the leading hole;
   the leading hole is disposed on the surrounding bottom board; and the leading hole and the inlet of the shell are both disposed on a side of the continuous positive airway pressure device.

3. The continuous positive airway pressure device as claimed in claim 2, wherein the leading board has two opposite side surfaces;
   one of the two opposite side surfaces of the leading board is disposed toward the leading hole, is defined as a central surface, and is a convex surface curved toward the leading hole;
   the central surface has a central line configured to define an imaginary vertical surface; and
   a first angle is defined between the imaginary vertical surface and the other one of the two opposite side surfaces of the leading board and is between 70 degrees and 89 degrees.

4. The continuous positive airway pressure device as claimed in claim 3, wherein the leading board has two end surfaces;
   the central surface is disposed between the two end surfaces;
   each one of the two end surfaces extends outward from a respective one of two opposite side edges of the central surface;
   each one of the two end surfaces is configured to define a second angle between the central surface and said end surface; and
   the second angle is between 90 degrees and 140 degrees.

5. The continuous positive airway pressure device as claimed in claim 1, wherein the continuous positive airway pressure device has a fluid rectifier being a hollow tube and disposed in the airflow passage.

6. The continuous positive airway pressure device as claimed in claim 2, wherein the continuous positive airway pressure device has a fluid rectifier being a hollow tube and disposed in the airflow passage.

7. The continuous positive airway pressure device as claimed in claim 3, wherein the continuous positive airway pressure device has a fluid rectifier being a hollow tube and disposed in the airflow passage.

8. The continuous positive airway pressure device as claimed in claim 4, wherein the continuous positive airway pressure device has a fluid rectifier being a hollow tube and disposed in the airflow passage.

9. The continuous positive airway pressure device as claimed in claim 5, wherein the fluid rectifier has multiple surrounding walls disposed in an interior of the fluid rectifier; and
   the multiple surrounding walls are arranged at spaced intervals and divide the interior of the fluid rectifier into multiple passages.

10. The continuous positive airway pressure device as claimed in claim 6, wherein the fluid rectifier has multiple surrounding walls disposed in an interior of the fluid rectifier; and
   the multiple surrounding walls are arranged at spaced intervals and divide the interior of the fluid rectifier into multiple passages.

11. The continuous positive airway pressure device as claimed in claim 7, wherein the fluid rectifier has multiple surrounding walls disposed in an interior of the fluid rectifier; and
   the multiple surrounding walls are arranged at spaced intervals and divide the interior of the fluid rectifier into multiple passages.

12. The continuous positive airway pressure device as claimed in claim 8, wherein the fluid rectifier has multiple surrounding walls disposed in an interior of the fluid rectifier; and the multiple surrounding walls are arranged at spaced intervals and divide the interior of the fluid rectifier into multiple passages.

13. The continuous positive airway pressure device as claimed in claim 9, wherein the continuous positive airway pressure device has at least one detector disposed to the fluid rectifier and configured to detect a flow volume and a flow velocity of an airflow in the fluid rectifier.

14. The continuous positive airway pressure device as claimed in claim 10, wherein the continuous positive airway pressure device has at least one detector disposed to the fluid rectifier and configured to detect a flow volume and a flow velocity of an airflow in the fluid rectifier.

15. The continuous positive airway pressure device as claimed in claim 11, wherein the continuous positive airway pressure device has at least one detector disposed to the fluid rectifier and configured to detect a flow volume and a flow velocity of an airflow in the fluid rectifier.

16. The continuous positive airway pressure device as claimed in claim 12, wherein the continuous positive airway pressure device has at least one detector disposed to the fluid rectifier and configured to detect a flow volume and a flow velocity of an airflow in the fluid rectifier.

17. The continuous positive airway pressure device as claimed in claim 2, wherein the partition has a heat dissipating hole defined through the partition; and a position of the heat dissipating hole corresponds to a position of the blower.

* * * * *